(12) United States Patent
Uitterlinden et al.

(10) Patent No.: US 6,808,881 B1
(45) Date of Patent: Oct. 26, 2004

(54) METHOD FOR DETERMINING SUSCEPTIBILITY TO HEART DISEASE BY SCREENING POLYMORPHISMS IN THE VITAMIN D RECEPTOR GENE

(75) Inventors: Andreas Gerardus Uitterlinden, Poortugaal (NL); Johannes Petrus Thomas Maria Van Leeuwen, Amstelveen (NL); Huibert Adriaan Pieter Pols, Papendrecht (NL)

(73) Assignee: Erasmus Universiteit Rotterdam, Rotterdam (NL)

( * ) Notice: Subject to any disclaimer, the term of this patent is extended or adjusted under 35 U.S.C. 154(b) by 0 days.

(21) Appl. No.: 09/786,992
(22) PCT Filed: Sep. 10, 1999
(86) PCT No.: PCT/EP99/07720
§ 371 (c)(1),
(2), (4) Date: May 30, 2001
(87) PCT Pub. No.: WO00/15840
PCT Pub. Date: Mar. 23, 2000

(30) Foreign Application Priority Data

Sep. 10, 1998 (GB) ............................................. 9819764

(51) Int. Cl.$^7$ ........................... C12Q 1/68; C12P 19/34; C07H 21/02; C07H 21/04
(52) U.S. Cl. ........................ 435/6; 435/91.1; 435/91.2; 536/23.1; 536/23.5; 536/24.31; 536/24.33; 536/24.1
(58) Field of Search ......................... 435/6, 91.1, 91.2; 536/23.1, 24.1; 514/44

(56) References Cited

FOREIGN PATENT DOCUMENTS

| WO | WO9403633 A | | 2/1994 | |
|---|---|---|---|---|
| WO | WO9740187 A | | 10/1997 | |
| WO | WO97/40187 | * | 10/1997 | ............ C12Q/1/68 |

OTHER PUBLICATIONS

Carling et al, 1997, Jrnl of Clinical Endocrinology and Metabolism, vol. 82, No. 6 p. 1772.*
Boucher, "Inadequate Vitamin D Status: Does it Contribute to the Disorders Comprising Syndrome 'X'," *British Journal of Nutrition*, 79:317, 319, 321 (1998).
Brunvand et al., "Congestive Heart Failure by Vitamin D Deficiency," *Acta Paaediatr*, 84:106–108 (1995).
Carling et al., "Vitamin D Receptor Genotypes in Primary Hyperparathyroidism," *Nature Medicine*, 1(12):1309–1310 (1995).
Haussler et al., "The Vitamin D Hormone and its Nuclear Receptor: Molecular Actions and Disease States," *J. Endocrinology*, 54:S57–S73 (1997).
Holick, M.F., "Noncalcemic Actions of 1, 25–Dihydroxyvitamin D3 Clinical Applications," *Bone* (GB, Pergamon Press, Oxford), 17(2):107S–111S (1995).
Scragg et al., "Myocardial Infarction is Inversely Assocated with Plasma 25–Hydroxyvitamin D3 Levels: A Community–Based Study," *Int. J. Epidemiology*, 19(3):559–563 (1990).
Uitterlinden et al., "A Large Scale Population Based Study of the Association of Vitamin D Receptor Gene Polymorphisms with Bone Mineral Density," *Journal of Bone and Mineral Research*, 11(9):1241–1248 (1996).
Van Schooten et al., "Putative Susceptibility Markers of Coronary Artery Disease: Association Between VDR Genotype, Smoking, and Aromatic DNA Adduct Levels in Human Right Atrial Tissue," *The FASEB Journal*, 12:1409–1417 (1998).
Carling et al., "Vitamin D Receptor Polymorphisms Correlate to Parathyroid Cell Function in Primary Hyperthyroidism," *JCME&E*, 82(6):1772–1775 (1997).
Carling et al., "Vitamin D Receptor (VDR) and Parathyroid Hormone Messenger Ribonucleic Acid Levels Correspond to Polymorphic VDR Alleles in Human Parathyroid Tumors," *JCE&E*, 83(7):2255–2259 (1998).
Vintzileos, A.M. et al., "Fetal Atrial Flutter and X–linked Dominant Vitamin D Resistant Rickets," *Obstet. Gynocol.*, 65:39S–44S (1985).
Kessel L., "Sick Sinus Syndrome Cured by Vitamin D?," *Geriatrics*, 45:83–85 (1990).
O'Connell, T.D. et al., "Regulation of Myosin Isozyme Expression by Vitamin D3 deficiency and 1,25–dihydroxyvitamin D3 in the Rat Heart," *Endocrinology*, 134:899–905 (1994).
Weishaar, R.E. et al., "Involvement of Vitamin D3 with Cardiovascular Function III. Effects on Physical Morphological Properties," *Am. J. Physiol.*, 258(Endocrinol. Metab. 21):E134–E142 (1990).
Weishaar, R.E. et al., "Involvement of Vitamin D3 with Cardiovascular Function II. Direct and Indirect Effects," *Am. J. Physiol.*, 253(Endocrinol. Metab. 16):E675–E683 (1987).
Weishaar, R.E. et al., "Vitamin D3 and Cardiovascular Function in Rats," *J. Clin. Invest.*, 79:1706–1712 (1987).

* cited by examiner

Primary Examiner—Carla J. Myers
Assistant Examiner—Sally Sakelaris
(74) Attorney, Agent, or Firm—Christensen O'Connor; Johnson Kindness PLLC (57) ABSTRACT

The present invention relates to prognostic method and means for determining susceptibility to heart disease in a subject by screening for polymorphisms in the Vitamin D receptor gene. In particular, the present invention provides a method for determining susceptibility to heart disease, the method comprising analysing the genetic material of a subject to determine which of the B/b, A/a or T/t alleles of the restriction enzyme sites BsmI, ApaI and TaqI respectively are present. Specific combinations of alleles represent a haplotype which is associated with susceptibility to heart disease.

4 Claims, 5 Drawing Sheets

TABLE 1.
Characteristics of the Population According to VDR Genotype

| CHARACTERISTIC† | VDR GENOTYPE | | | | | P-VALUE |
|---|---|---|---|---|---|---|
| | 11 | 12 | 13 | 22 | 23 | 33 | |
| Number (%) | 493 (24.9) | 735 (37.2) | 202 (10.2) | 351 (17.7) | 170 (8.6) | 27 (1.4) | |
| Age (years) | 67.0 ± 6.8 | 67.1 ± 6.8 | 67.2 ± 7.1 | 67.0 ± 7.1 | 66.9 ± 6.8 | 67.0 ± 7.1 | 0.93§ |
| Body Mass Index (kg/m$^2$) | 26.1 ± 3.7 | 26.0 ± 3.3 | 25.8 ± 3.6 | 26.1 ± 3.4 | 26.0 ± 3.2 | 25.5 ± 2.9 | 0.78 |
| Dietary calcium-intake (mg/day) | 1116 ± 350 | 1122 ± 364 | 1122 ± 356 | 1092 ± 369 | 1094 ± 342 | 1158 ± 254 | 0.78 |
| Serum HDL-cholesterol (mmol/l) | 1.34 ± 0.37 | 1.35 ± 0.36 | 1.36 ± 0.34 | 1.35 ± 0.37 | 1.32 ± 0.33 | 1.36 ± 0.38 | 0.91 |
| Serum cholesterol (mmol/l) | 6.68 ± 1.21 | 6.63 ± 1.26 | 6.64 ± 1.16 | 6.60 ± 1.19 | 6.59 ± 1.21 | 6.60 ± 0.96 | 0.95 |
| Current Smokers (%) | 130 (26.4) | 172 (23.4) | 45 (22.3) | 78 (22.2) | 40 (23.5) | 6 (22.2) | 0.83¶ |

† Values are means ± standard deviation; BMI is weight divided by the square height § P-value for ANOVA ¶ P-value for Chi-2 test

TABLE 2.
Myocardial Infarction According to *VDR allele 1* Genotype

|  | Men | | Women | | All | |
|---|---|---|---|---|---|---|
|  | MI (%) | Total | MI (%) | Total | MI (%) | Total |
| Total | 151 (15.8) | 954 | 62 (6.1) | 1024 | 213 (10.8) | 1978 |
| by *VDR allele 1* genotype | | | | | | |
| Reference† | 39 (14.7) | 266 | 10 (3.5) | 282 | 49 (8.9) | 548 |
| Heterozygotes | 69 (15.4) | 449 | 31 (6.4) | 488 | 100 (10.7) | 937 |
| Homozygotes | 43 (18.0) | 239 | 21 (8.3) | 254 | 64 (13.0) | 493 |
| $\chi^2$ | 1.18 | | 5.38 | | 4.43 | |
| P-VALUE | 0.55 | | 0.07 | | 0.11 | |

Odds Ratios for Myocardial Infarct by VDR allele 1 genotype [95% CI]

| Crude | | | |
|---|---|---|---|
| Reference | 1.00 | 1.00 | 1.00 |
| Heterozygotes | 1.07 [0.72 - 1.71] | 1.86 [0.90 - 3.85] | 1.23 [0.86 - 1.76] |
| Homozygotes | 1.28 [0.80 - 2.05] | 2.48 [1.15 - 5.39] | 1.53 [1.03 - 2.27] |
| per copy *VDR 1* allele | 1.13 [0.89 - 1.44] | 1.53 [1.07 - 2.20] | 1.24 [1.02 - 1.51] |
| Age-, BMI-adjusted | | | |
| Reference | 1.00 | 1.00 | 1.00 |
| Heterozygotes | 1.11 [0.72 - 1.71] | 1.77 [0.85 - 3.68] | 1.22 [0.85 - 1.75] |
| Homozygotes | 1.33 [0.82 - 2.14] | 2.45 [1.12 - 5.34] | 1.55 [1.04 - 2.30] |
| per copy *VDR 1* allele | 1.15 [0.91 - 1.47] | 1.53 [1.06 - 2.22] | 1.25 [1.02 - 1.52] |

† "Reference" includes VDR genotypes 22, 23, 33; "Heterozygotes" includes 12, 13; "Homozygotes" includes 11

TABLE 3.

Myocardial Infarction According to VDR allele 1 Genotype by Quartiles of Dietary Calcium Intake

| | < 877 mg/day | | > 877, < 1076 | | > 1076, < 1302 | | ≥ 1302 | |
|---|---|---|---|---|---|---|---|---|
| | MI (%) | Total | MI (%) | Total | MI (%) | Total | MI (%) | Total |
| Total | 43 (10.0) | 432 | 50 (11.6) | 431 | 45 (10.4) | 432 | 49 (11.4) | 430 |
| by VDR allele 1 genotype | | | | | | | | |
| Reference† | 13 (9.9) | 131 | 14 (12.5) | 112 | 12 (9.6) | 125 | 3 (2.6) | 114 |
| Heterozygotes | 21 (10.5) | 200 | 24 (11.8) | 204 | 21 (10.0) | 210 | 26 (12.6) | 207 |
| Homozygotes | 9 (8.9) | 101 | 12 (10.4) | 115 | 12 (12.4) | 97 | 20 (18.3) | 109 |
| $\chi^2$ | 0.19 | | 0.25 | | 0.53 | | 14.17 | |
| P-VALUE | 0.91 | | 0.88 | | 0.77 | | 0.0008 | |

Odds Ratios for Myocardial Infarct by VDR allele 1 genotype [95% CI]

| | | | | | | | | |
|---|---|---|---|---|---|---|---|---|
| Crude | | | | | | | | |
| Reference | 1.00 | | 1.00 | | 1.00 | | 1.00 | |
| Heterozygotes | 1.09 [0.52 - 2.27] | | 0.93 [0.46 - 1.89] | | 1.04 [0.49 - 2.20] | | 5.40 [1.59 - 18.3] | |
| Homozygotes | 0.90 [0.37 - 2.20] | | 0.82 [0.36 - 1.87] | | 1.32 [0.56 - 3.09] | | 8.31 [2.39 - 29.0] | |

† "Reference" includes VDR genotypes 22, 23, 33; "Heterozygotes" includes 12, 13; "Homozygotes" includes 11

TABLE 4.

Myocardial Arrythmias According to VDR allele 1 Genotype by Quartiles of Dietary Calcium Intake

|  | < 877 mg/day | | > 877, <1076 | | > 1076, <1302 | | ≥ 1302 | |
|---|---|---|---|---|---|---|---|---|
|  | MA (%) | Total | MA (%) | Total | MA (%) | Total | MA (%) | Total |
| Total | 37 (12.1) | 307 | 27 (9.2) | 292 | 17 (5.6) | 302 | 31 (10.1) | 306 |
| by VDR allele 1 genotype | | | | | | | | |
| Reference† | 16 (17.0) | 94 | 6 (8.8) | 68 | 7 (7.7) | 91 | 5 (5.7) | 88 |
| Heterozygotes | 14 (10.1) | 138 | 14 (10.1) | 138 | 6 (4.4) | 135 | 12 (8.5) | 141 |
| Homozygotes | 7 (9.3) | 75 | 7 (8.1) | 86 | 4 (5.3) | 76 | 14 (18.2) | 77 |
| $\chi^2$ | 3.19 | | 0.27 | | 1.11 | | 7.80 | |
| P-VALUE | 0.20 | | 0.87 | | 0.58 | | 0.02 | |

Odds Ratios for Myocardial arrythmias by VDR allele 1 genotype [95% CI]

| Crude | | | | | | | | |
|---|---|---|---|---|---|---|---|---|
| Reference | 1.00 | | 1.00 | | 1.00 | | 1.00 | |
| Heterozygotes | 0.57 [0.26 - 1.23] | | 1.13 [0.41 - 3.12] | | 0.54 [0.18 - 1.69] | | 1.60 [0.54 - 4.74] | |
| Homozygotes | 0.51 [0.20 - 1.32] | | 0.92 [0.29 - 2.92] | | 0.69 [0.19 - 2.46] | | 3.63 [1.22 - 10.9] | |

† "Reference" includes VDR genotypes 22, 23, 33; "Heterozygotes" includes 12, 13; "Homozygotes" includes 11

FIG. 1

SEQUENCE LISTING

<160> NUMBER OF SEQ ID NOS: 2

<210> SEQ ID NO 1
<211> LENGTH: 30
<212> TYPE: DNA

-continued

```
<213> ORGANISM: Artificial Sequence
<220> FEATURE:
<221> NAME/KEY: misc_feature
<223> OTHER INFORMATION: primer

<400> SEQUENCE: 1
caaccaagac tacaagtacc gcgtcagtga                              30

<210> SEQ ID NO 2
<211> LENGTH: 24
<212> TYPE: DNA
<213> ORGANISM: Artificial Sequence
<220> FEATURE:
<221> NAME/KEY: misc_feature
<223> OTHER INFORMATION: primer

<400> SEQUENCE: 2
gcaactcctc atggctgagg tctc                                    24
```

METHOD FOR DETERMINING SUSCEPTIBILITY TO HEART DISEASE BY SCREENING POLYMORPHISMS IN THE VITAMIN D RECEPTOR GENE

The present invention relates to a prognostic method and prognostic means based on polymorphisms in the vitamin D receptor gene. In particular, the present invention relates to a method for determining susceptibility to heart disease by screening for polymorphisms in the vitamin D receptor gene.

Heart disease such as myocardial infarction is a complex phenotype caused by interaction of a number of genetic and environmental factors.[1] Advances in molecular genetics have led to the identification of a number of genetic risk factors for heart disease, such as gene variants involved in thrombosis[2,3] and lipid metabolism[4]. However, another important risk factor for heart disease such as myocardial infarction is a deregulated calcium homeostasis which is required for maintenance of neuromuscular activity[5]. Disturbances of the calcium balance have been implicated in hypertension, ventricular hypertrophy, aortic calcification and arrythmnias all of which are important risk factors associated with myocardial infarction.

Vitamin D is a potent regulator of bone and calcium homeostasis, as well as of cellular differentiation and replication in many tissues, and mediates its effects through the vitamin D receptor (VDR). Cloning of the vitamin D receptor has shown it to be a member of the ligand-activated superfamily, which are natural regulators of a number of physiological and developmental processes. The major physiological function of the active metabolite of vitamin D, i.e. $1,25(OH)_2D_3$, is to maintain serum calcium levels in the normal range. This is accomplished by stimulating the small intestine to increase it's efficiency of absorbing calcium from the diet and to mobilize calcium stores from bone. The action of the hormone is mediated by the vitamin D receptor (VDR), a steroid transcription factor that mediates hormone response by initiating gene transcription and mRNA translation[6]. Involvement of the vitamin D endocrine system in the etiology of heart disease was suggested by epidemiological studies which found serum levels of 25-hydroxyvitamin $D_3$ to be reduced in myocardial infarcton patients compared with control individuals[7]. Furthermore, congestive hean failure associated with vitamin D deficiency has been described in a three and a half month old child[8]. The involvement of the vitamin D endocrine system in cardiac arrythria was suggested by case reports involving the observation of atrial flutter in a foetus with X-linked vitamin D resistant rickets[9] and sick sinus syndrome that was cured by administration of vitamin D to a 77-year old caucasian woman[10]. Further studies in the rat have also demonstrated an important role of the vitamin D endocrine system in cardiovascular function, wherein vitamin D3-deficiency can lead to large increases in the contracile function of the heart[17-20].

The above studies establish a link between the via D endocrine system and risk of heart disease in an individual. Further studies (Carling et al, JCE&M, 82 (6) 1772–1775 (1997); Carling et al, Nature Medicine, 1 (12) 13099–1310 (1995) and Carling et al, JCE&M 83 (7) 2255–2259 (1998) show an association between the b, a and T alleles of the vitamin D receptor gene and hyperparathyroidism. Hypertension is considered to be a feature of hyperparathyroidism (Boucher, B. J, of Nutr., 79 315–327 (1998). However, the genetic component of heart disease such as myocarlial infarction or cardiac arrythmia is poorly defined. As a result, methods of diagnosing risk of heart disease, or treating those suffering from heart disease, are restricted.

Thus, in a first aspect of the present invention, there is provided a method of determining susceptibility to heart disease in a subject, said method comprising analysing genetic material of a subject to determine which allele(s) of the vitamin D receptor is/are present.

Figure 1:
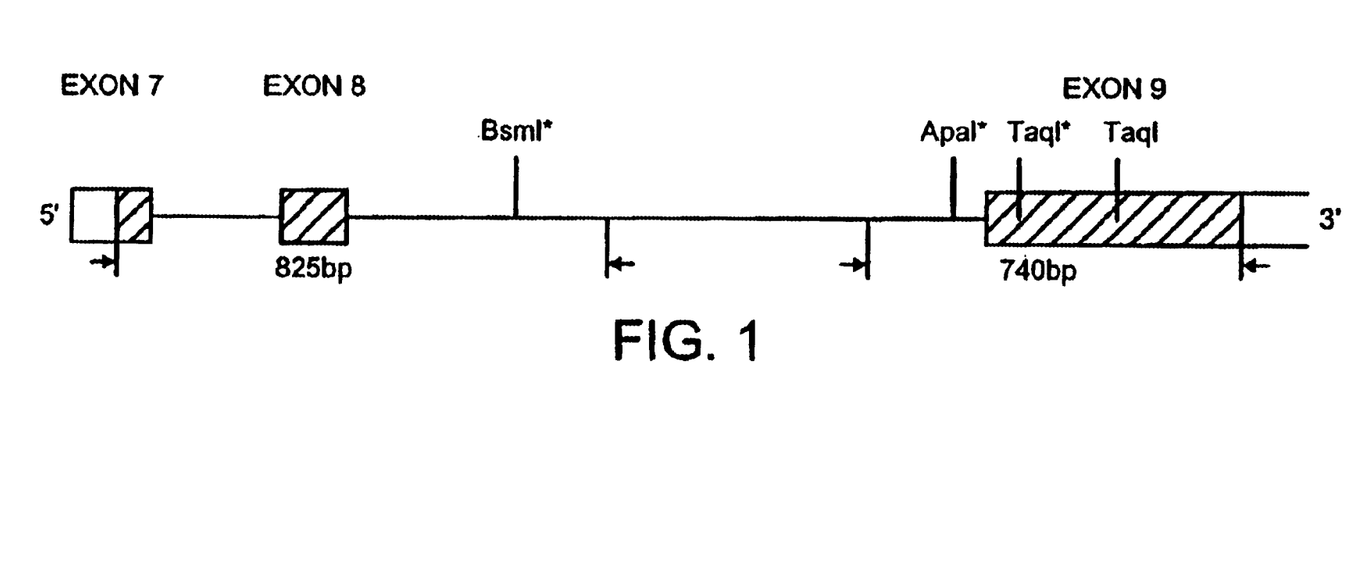
FIG. 1 is a schematic presentation of the region between exon 7 and the 3' UTR of the vitamin D receptor gene.

The vitamin D receptor gene (12q12) comprises inherited polymorphisms between exon 7 and the 3' UTR of the VDR gene. as shown in FIG. 1. These alleles are denoted B/b, A/a and T/t for restriction enzyme sites BsmI, ApaI and TaqI respectively (or enzymatic or chemical procedures with similar specificities), where a lower case letter denotes the presence of a wild type restriction site which is capable of being cleaved, and a capital letter denotes the presence of a mutant restriction enzyme site which is not capable of being cleaved by the relevant restriction enzyme. For the purposes of the present invention, determination of which alleles are present in a particular gene may be referred to as determining the genotype of a subject for a particular gene. It is apparent from the above that each copy of the vitamin D receptor gene will comprise a specific combination of the three alleles, this combination being referred to as the haplotype of the gene. For example, the haplotype may be baT, indicating the presence of cleavable BsmI and ApaI sites, and a non-cleavable TaqI site. Direct haplotyping of the VDR gene has allowed five different haplotypes to be determined, of which three are common.[16]

The present invention is based on the discovery of a genetic component of heart disease. It has now been shown that presence of the b, a or T alleles, and in particular the baT haplotype of the vitamin D receptor is/are associated with increased risk of heart disease. Thus, the presence of such alleles of the vitamin D receptor gene may be used to determine susceptibility to heart disease.

Preferably, the method of the first aspect of the present invention comprises the additional step of determining whether the alleles present are associated with risk of heart disease. This may be performed by comparing the alleles present in the genetic material of the subject with genotypes of the vitamin D receptor having known degrees of risk of heart disease. For example, a visual aid detailing alleles and their relative risk of heart disease may be used to determine whether the genotype of the subject is associated with a high or low risk of heart disease.

The first aspect of the present invention may also comprise the additional step of determining aspects of calcium metabolism, such as calcium levels, in a subject. Preferably, the daily calcium intake is measured. This feature of the first aspect is based on the observation that the correlation between vitamin D receptor genotype and heart disease may be dependent upon dietary calcium intake.

The method of the first aspect may be performed in vitro. Preferably, the method is performed on tissue or fluid removed from the body of the subject. Thus, the present invention relates to a non-invasive method, the results of which provide an indication of susceptibility to heart disease but do not lead to a diagnosis upon which an immediate medical decision regarding treatment has to be made.

The present invention may be performed on any subject for whom it is desirable to determine risk of heart disease. Preferably, the subject may be a mammal. Most preferably, the method of the first aspect is performed on humans, preferably male.

Heart disease may include atrial or ventricular hypertrophy, aortic calcification, arrythmina, hypertension, and most importantly, myocardial infarction.

In a preferred feature of the first aspect of the present invention, there is provided a method of determining susceptibility to heart disease, said method comprising analysing genetic material of a subject to determine which of the B/b, A/a or T/t alleles of the vitamin D receptor gene is/are present. The method may comprise determining whether one or more of the above alleles is present. The subject may further be classified as being heterozygous or homozygous for one or more alleles. Preferably, the method comprises the additional step of determining whether the allele(s) present is/are associated with risk of heart disease, wherein presence of the b, a or T alleles is associated with increased risk of heart disease. Homozygosity for the a, b or T allele may further increase the susceptibility to heart disease in a subject.

In a preferred feature of the first aspect, there is provided a method of determining susceptibility to heart disease in a subject, said method comprising analysing the genetic material of a subject to determine the haplotype of the BsmI, ApaI and TaqI alleles at the vitamin D receptor. Preferably, said method comprises determining whether the haplotype of the subject is associated with risk of heart disease, wherein the haplotype baT is associated with high risk of heart disease. A subject homozygous for said haplotype may be at a higher risk of heart disease than those heterozygous for the haplotype.

In a preferred feature of the first aspect, there is provided a method of determining susceptibility to heart disease, said method comprising the additional step of determining the copy number of the B/b, A/a or T/t alleles or haplotype of the vitamin D receptor, where an increase in copy number is associated with increased risk of heart disease.

The present invention may be performed using any suitable method known in the art. Preferably, a tissue or fluid sample is first removed from a subject. Examples of suitable samples include blood, mouth or cheek cells, and hair samples containing roots. Other suitable samples would be known to the person skilled in the art. The genetic material is then extracted from the sample for diagnosis, using any suitable method. The genetic material may be DNA or RNA, although preferably DNA is used. For example, the DNA may be extracted using the technique described in Sambrook et al (Molecular Cloning—A Laboratory Manual, Cold Spring Harbor Laboratory Press). Determination of the genotype of a subject may then be carried out using the extracted DNA, employing any one of the following techniques:

Southern blot analysis following digestion with one or more appropriate restriction enzymes.

PCR amplification followed by digestion with one or more appropriate restriction enzymes and, optionally, separation of digestion products by gel electrophoresis.

Sequencing of a relevant gene fragment by any suitable method.

Visualization of heteroduplex patterns, for example on PAA or agarose gels, where different patterns may indicate the presence of one or more specific alleles.

Separation of DNA fragments using denaturing gradient gels, wherein the degree of separation will depend upon the presence or absence of one or more polymorphic restriction sites.

Separation using SSCP analysis, the patterns of which will depend upon the presence or absence of one or more polymorphic restriction sites.

Use of allele specific oligonucleotides, hybridization patterns of which will be specific for various combinations of alleles.

Methods such as OLA, Taqman or dot-blot for the detection of known mutations.

Visualization of DNA sites using fluorescent labelled probes for alleles of interest.

RFLP analysis

Where it is desirable to use particular restriction enzymes in performing the present invention, the skilled person will understand that enzymatic or chemical procedures having similar specificities may also be used. For example, restriction enzymes having similar specificity (isoschizomers) to those described herein may be used, or chemical degradation procedures with DNA or RNA cutting specificity.

Other techniques suitable for determining the genotype of a subject may be used in the present invention.

Where the haplotype of a gene is to be determined, it is preferable to use a direct haplotyping method, as described in Uitterlinden et al[16]. In such a method, the relevant portion of the gene is amplified and then subjected to restriction enzyme digestion, in order to determine the presence or absence of restriction enzyme sites. Thus, for example, where the haplotype of the vitamin D receptor gene is to be determined, the portion of the gene between exon 7 and the 3' UTR may be amplified, and the amplified DNA digested with the BsmI, ApaI or TaqI restriction enzymes. Gel analysis may then be used to determine which alleles are present.

Preferably, a fragment may be amplified using polymerase chain reaction (PCR) techniques, to produce copies which, where the fragment is of the vitamin D receptor, are at least 1000 base pairs in length, and most preferably at least 1800 base pairs in length. PCR techniques are well known in the art, and it is within the ambit of the skilled person to identify primers for amplification of the appropriate region of the above genes, namely the region from exon 7 to the 3' UTR of the vitamin D receptor gene. PCR techniques are described in EP-A-0200362 and EP-A-0201184.

In a preferred feature of the first aspect, there is provided a method of determining susceptibility to heart disease in a subject, said method comprising amplifying a fragment comprising a portion of the region from exon 7 to the 3' UTR of the vitamin D receptor gene, and determining which allele(s) in the vitamin D receptor is/are present. Primers suitable for amplification of said portion of the vitamin D receptor gene would be readily available to a person skilled in the art. Examples of such primers include:

5'-CAACCAAGACTACAAGTACCGCGTCAGTGA-3'(SEQ ID NO:1) 1.

and/or

5'GCAACTCCTCATGGCTGAGGTCTC-3'(SEQ ID NO:2) 2.

Where the amplified portion of the gene is larger than the above defined portion of the vitamin D receptor gene containing the relevant alleles, it is preferable to avoid the inclusion of gene sequences which comprise any one of the BsmI, ApaI or TaqI restriction sites.

In a second aspect of the present invention, there is provided a method of therapy, said method comprising treating a subject diagnosed as being at risk of heart disease, to reduce the risk of heart disease. Preferably, the subject is diagnosed as being at risk of heart disease in accordance with the first aspect of the present invention.

Therapy may in the form of preventative or palliative care. Suitable treatments include modifications to lifestyle, regular exercise and changes in diet. Suitable treatments, including pharmaceutical preparations, would be known to physicians and persons skilled in the art. Examples include ACE inhibitors, beta-blockers, calcium or vitamin D preparations, magnesium sulphate, thrombolytics and analgeasics.

In a third aspect of the present invention, there is provided a method of predicting the response of a subject to treatment, said method comprising analysing genetic material of a subject to determine which allele(s) of the vitamin D receptor gene is/are present. Preferably, the method includes first determining whether the subject is susceptible to heart disease. Where a subject has been determined as susceptible to heart disease, the method may further comprise administering the appropriate treatment. The present aspect of the invention is based on the observation that agents, such as calcium channel blockers, which are useful for treatment of a variety of cardiovascular diseases may also be associated with cardiovascular morbidity in some cases. The effect of an agent may therefore depend on the underlying cause of the heart disease. For example, the presence of the b, a or T alleles of the vitamin D receptor may result in modification of calcium uptake, leading to impaired cardiovascular function. Thus, in such a case it would be preferable to avoid the use of calcium channel blocking agents.

In a fourth aspect of the present invention, there is provided use of a kit to determine which allele(s) of the vitamin D receptor gene is/are present, said kit comprising (i) one or more nucleic acid primer molecules for amplification of a portion of the vitamin D receptor gene, and (ii) means for determining which allele(s) is/are present in said gene.

Preferably, the primer molecules are suitable for amplification of at least a portion of the region between exon 7 and the 3'UTR of the vitamin D receptor gene. Examples of suitable primers are described above.

Means for determining which allele(s) is/are present in the vitamin D receptor gene, may include any reagents or molecules necessary for use in any of the methods described above. For example, where PCR followed by DNA digestion is used, said means preferably include PCR reagents and one or more of the BsmI, ApaI, or TaqI restriction enzymes. Where the method employs Southern Blotting, heteroduplex visualization, or fluorescent labelling techniques for example, probes which bind to the appropriate regions of the vitamin D receptor gene may be included. Where necessary, such probes may be labelled to allow detection, for example by nick-translation, radio- or fluorescent-labelling, or random primer extension whereby the non-labelled nucleotides serve as a template for the synthesis of labelled molecules. Other methods of labelling probes are well known in the art.

In a preferred feature of the fourth aspect of the present invention, there is provided use of a kit further comprising means for indicating correlation between the genotype of a subject and risk of heart disease. Said means may be in the form of a chart or visual aid, which indicate that presence of the b, a or T alleles or baT haplotype of the vitamin D receptor is/are associated with heart disease such as cardiac arrythmia or myocardial infarction.

In a fifth aspect of the present invention, there is provided a kit for determining risk of heart disease in a subject, said kit comprising (i) one or more nucleic acid primer molecules for amplification of a portion of the vitamin D receptor gene; (ii) means for determining which allele(s) is/are present in said gene; and (iii) means for indicating correlation between the allele(s) and risk of heart disease.

In a preferred feature of the fifth aspect, the kit may also comprise DNA control samples, for comparison with DNA sequences of a subject. The control samples may comprise the sequence of one or more alleles of the vitamin D receptor gene, or may comprise the sequence of various haplotypes.

Preferred features of each aspect of the present invention are as for each other aspect, mutatis mutandis.

The present invention will now be described in detail with reference to the following examples and FIGURE.

EXAMPLE 1

Relationship between alleles of the vitamin D receptor gene and myocardial infarction, cardiac arrythmias and dietary calcium intake in the elderly

METHODS

Study Subjects

The Rotterdam Study is a population-based cohort study of 7983 subjects aged 55 or more years, residing in the Ommoord district of the city of Rotterdam in the Netherlands. The study was designed to document the occurrence of disease in the elderly in relation to several potential determinants.[15] A total of 10,275 persons, of whom 9161 (89 percent) were living independently, were invited to participate in the study in 1991. In the independently living subjects, the overall response rate was 77 percent for home interview and 71 percent for examination in a research centre, including measurement of anthropometric characteristics and blood sampling. The Rotterdam Study was approved by the Medical Ethics Committee of the Erasmus University Medical School and written informed consent was obtained from each subject.

The analysis of the association between VDR genotype, myocardial infarction and arrytmias was performed in a subgroup of men and women participating in the study. Baseline measurements, collected from 1990–1993, included and electrocardiogram (ECG), history of cardiovascular disease, established cardiovascular risk factors, and use of medication. A digitally stored ECG was available for 5931 independently living subjects from the study, but 1453 of these were excluded on the basis of age (>80 yrs), use of a walking aid, diabetes mellitus or use of diuretic, estrogen, thyroid hormone or cytostatic drug therapy. From the 4478 remaining subjects, we studied a random sample of 2000 men and women aged 55 to 80 years. ECG data or DNA samples were not available for 22 subjects, resulting in a final study group of 1978 subjects.

Measurements

Height and weight were measured at the initial examination in a standing position without shoes. Myocardial infarction, including so called silent myocardial infarctions, was confirmed by ECG analysis. For 1725 men and women (87%) data was available on dietary intakes of calcium (mg/day) during the preceding year. These were assessed by food frequency questionnaire and adjusted for energy intake. Age at menopause and current cigarette smoking were assessed by questionnaire. Cardiac arrythmias were diagnosed by ECG analysis and included the occurrence of sinus irregularities, atrial flutter, and atrial fibrillation and were recorded, confirmed and classified by a physician. For 976 subjects data on cardiac arrythmias were available (49%). Of these subjects, data on dietary calcium intake were available for 899 subjects (92%).

Determination of VDR Genotypes

Genomic DNA was extracted from peripheral venous blood samples according to standard procedures and the anonymous polymorphisms were detected by PCR as previously described[16]. Three anonymous polymorphic restriction enzyme recognition sites at the 3' end of die VDR gene, i.e. for BsmI, ApaI, and TaqI, were assessed in relation to each other by a direct molecular haplotyping PCR procedure which we developed[16]. This allows us to determine ophase of the alleles at each of the RFLP loci and as a result three frequent haplotype alleles are discerned, encoded 1 (baT; frequency 48%), 2 (BAt; frequency 40%), 3 (bAT; frequency 10%) combining to six genotypes encoded 11, 12, 13, 22, 23, and 33. Detailed information on haplotype alleles and genotype frequencies in the Rotterdam Study can be found elsewhere[16]. The PCR reaction mixture of 25 microliters contained 100 ng of genomic DNA, 50 mM KCl, 10 mnM Tris-HCl (pH 8.3), 1.5 mM $MgCl_2$, 0.2 mM dideoxynucleotidetriphosphates, 150 ng of each primer, and 0.2 unit of Super Taq polymerase (HT Biotechnology, Cambridge, UK). The reactions were performed in a DNA thermocycler (model 480, Perkin Elmer) with a cycling protocol of 94° C., 60° C., and 72° C. for 1 inin each, for 28 cycles. Ten microliters of PCR product were simultaneously digested with 5 units BsamI, 5 units ApaI, and 5 units TaqI restriction enzyme and 2 microliters of a 10x concentrated buffer (containing 150 inM Tris-HCl, pH 7.5, 250 mM NaCl, and 35 MM $MgCl_2$) by incubating for 30 min at 37° C., followed by a 30 min incubation at 65° C. The digestion products were analysed on a 1.2 percent agarose gel run in 44.5 MM Tris, 44.5 mM boric acid, 1 mnM $Na_2EDTA$) for 300 volt-hours. Separation patterns were documented by Polaroid photography under UV-illumination (302 nm). To confirm the accuracy of genotyping, repeat analysis was performed on 200 random samples. No discrepancies were found.

Statistical Analysis

Relevant clinical variables were compared between the genotype groups by analysis of covariance and multiple linear regression was used to adjust values for confounding factors such as age, anthropometric variables, smoking. For the comparisons we made reference, heterozygote and homozygote groups for each of the VDR alleles. For example, for VDR allelel the groups comprised 22, 23, and 33 for the reference group, 12, and 13 for the heterozygote group, and 11 for the homozygote group. The Chi-squared test was used to test for genotype distribution in men and women with and without myocardial infarction and with and without cardic arrythmias. Odds ratios (with 95 percent confidence interval) were calculated by multivariate logistic regression analysis to estimate the relative risk of myocardial infarction and cardiac arrythrnias. A multivariate regression model was designed to test for the influence of dietary calcium intake on the relationship between VDR genotype and myocardial infarction and VDR genotype with cardiac arrythmias. For this analysis, subjects were categorised into groups of calcium intake defined by quartiles of the population. An interaction term was included in the regression analysis defined as gene allele dose multiplied with calcium-intake. P values for all statistical tests were two-sided.

RESULTS

Characteristics of the Study Subjects

Anthropometric, and dietary measurements in the men and women with the six VDR genotypes are shown in Table 1. The allele frequencies (1=48.6%; 2=40.6%; and 3=10.8%) and the distribution of genotypes were similar to that reported in a previous study[22]. There was no difference with regard to age, dietary calcium intake, smoking habits, body mass index, serum HDL-cholesterol, and serum cholesterol in the six genotype groups.

Association with Myocardial Infarction

The distribution of myocardial infarction by VDR genotype in men and women is shown in Table 2. There was modest over-representation of both men and women carrying the VDR haplotype allele 1 as compared with subjects without the allele although this did not reach significance. Logistic regression analysis showed that subjects in the heterozygous group had a 1.2 fold increased risk for myocardial infarction and the subjects in the homozygous group had a 1.5-fold increased risk, as compared with subjects not carrying the VDR allele 1. The gene dose effect was 1.2-fold increased risk per copy of the VDR allele 1. The gene dose effect was larger for women when compared to men (RRs were 1.1 (95% confidence interval 0.9–1.4) for men and 1.5 (95% confidence interval 1.1–2.2) for women) but the interaction term of sex times genotype in the regression model was not significant (P=0.65). The relative risks for myocardial infarction did not change after adjustment for potential confounding factors such as age, body mass index and smoking in the regression analysis. For VDR haplotype allele 2 and haplotype allele 3 no significant differences were observed (data not shown).

Modification of the Association by Dietary Calcium Intake

When the study subjects were stratified according to quartiles of dietary calcium intake, the differences in distribution of myocardial infarction by VDR genotype were restricted to individuals with the highest intake of calcium (1302 mg/day or more). These differences corresponded with 5.4-fold increased risk for heterozygote carriers and 8.3-fold increased risk for homozygote carriers of VDR haplotype allele 1. Considering age, genotype and myocardial infarction together in a multivariate regression model, we found a significant modifying effect of dietary calcium intake on the VDR genotype effect on risk for myocardial infarction (P=0.04).

Association with Cardiac Arrythmias

We subsequently analysed the distribution of cardiac arrythmias by VDR genotype. We did not observe differences in the distribution of arrytmias by VDR genotype in the total study group. However, in the group with high calcium intake (1302 mg/day or more) there was significant over-representation of cardiac arrythrnias for subjects carrying the VDR haplotype allele 1 as compared with subjects without the allele 1 (Table 4).

Logistic regression analysis showed that subjects in the heterozygous group had a 1.6 fold increased risk for cardiac arrythmias and the subjects in the homozygous group had a 3.6-fold increased risk, as compared with subjects not carrying the VDR allele 1. The relative risks for cardiac arrythmia did not change after adjustment for potential confounding factors such as age, body mass index and smoking in the regression analysis. Also when myocardial infarction was entered into the model the relative risks did not change.

DISCUSSION

Polymorphisms of the vitamin D receptor gene are associated with the risk of myocardial infarction. The increased risk was especially notable in subjects with a high dietary calcium intake. In this group, we also observed VDR haplotype 1 to be associated with increased risk of cardiac arrythmnias. Cardiac arrythmias have been frequently observed following a myocardial infarct event. However, the VDR genotype dependent risk for cardiac arrythmias we observe, is independent of myocardial infarction. This indicates that the genotype effect we observe for myocardial infarction is not mediated by the genotype effect on cardiac arrythmias.

Our results indicate a genetic susceptibility of the risk for myocardial infarction and cardiac arrythmias in subjects with a relatively high dietary calcium intake. This strongly suggest that the VDR genotype effect on myocardial infarction and cardiac arrythmias is mediated by an effect on calcium transport. Treatment with calcium and vitamin D has been indicated for arrythmias and hypertrophy and has been shown to improve myocardial function.

The hormone vitamin D has been shown to influence the Ca-flux in a variety of cell types including heart muscle cells. These rapid effects of the hormone are suggested to involve a non-genomic pathway by which the plasmalemmal VDR is coupled to plasma membrane Ca2+ channel proteins.

Calcium channel blocking agents are indicated for the treatment of a variety of cardiovascular diseases, including cardiac arrythmias, but have also been found associated with increased cardiovascular morbidity[21,22]. Therefore, the modification by calcium intake of the VDR genotype dependent effect on myocardial infarction we observe opens the possibility that genotyping at the VDR gene locus might be of value in predicting the response to treatment with some of these drugs. Prospective clinical trials are needed to investigate the clinical and therapeutic implications of our results.

TABLE 1

Characteristics of the Population According to VDR Genotype

| CHARACTERISTIC[†] | VDR GENOTYPE | | | | | | P-VALUE |
| --- | --- | --- | --- | --- | --- | --- | --- |
| | 11 | 12 | 13 | 22 | 23 | 33 | |
| Number (%) | 493 (24.9) | 735 (37.2) | 202 (10.2) | 351 (17.7) | 170 (8.6) | 27 (1.4) | |
| Age (years) | 67.0 ± 6.8 | 67.1 ± 6.8 | 67.2 ± 7.1 | 67.0 ± 7.1 | 66.9 ± 6.8 | 67.0 ± 7.1 | 0.93[§] |
| Body Mass Index (kg/m$^2$) | 26.1 ± 3.7 | 26.0 ± 3.3 | 25.8 ± 3.6 | 26.1 ± 1.34 | 26.0 ± 3.2 | 25.5 ± 2.9 | 0.78 |
| Dietary calcium-intake (mg/day) | 1116 ± 350 | 1122 ± 364 | 1122 ± 356 | 1092 ± 369 | 1094 ± 342 | 1158 ± 254 | 0.78 |
| Serum HDL-cholesterol (mmol/l) | 1.34 ± 0.37 | 1.35 ± 0.36 | 1.36 ± 0.34 | 1.35 ± 0.37 | 1.32 ± 0.33 | 1.36 ± 0.38 | 3.91 |
| Serum cholesterol (mmol/l) | 6.68 ± 1.21 | 6.63 ± 1.26 | 6.64 ± 1.16 | 6.60 ± 1.19 | 6.59 ± 1.21 | 6.60 ± 0.96 | 0.95 |
| Current smoker (%) | 130 (26.4) | 172 (23.4) | 45 (22.3) | 78 (22.2) | 40 (23.5) | 6 (22.2) | 0.83[¶] |

[†]Values are means ± standard deviation; BMI is weight divided by the square height
[§]P-value for ANOVA
[¶]P-value for Chi-2 test

TABLE 2

Myocardial infarction According to VDR allele I Genotype

| | Men | | Women | | All | |
| --- | --- | --- | --- | --- | --- | --- |
| | MI (%) | Total | MI (%) | Total | MI (%) | Total |
| Total by VDR allele I genotype | 151 (15.8) | 954 | 62 (6.1) | 1024 | 213 (10.8) | 1978 |
| Reference[†] | 39 (14.7) | 266 | 10 (3.5) | 282 | 49 (8.9) | 548 |

TABLE 2-continued

Myocardial infarction According to VDR allele I Genotype

| | Men | | Women | | All | |
|---|---|---|---|---|---|---|
| | MI (%) | Total | MI (%) | Total | MI (%) | Total |
| Heterozygotes | 69 (15.4) | 449 | 31 (6.4) | 488 | 100 (10.7) | 937 |
| Homozygotes | 43 (18.0) | 239 | 21 (8.3) | 254 | 64 (13.0) | 493 |
| $x^2$ | 1.18 | | 5.38 | | 4.43 | |
| P-VALUE | 0.55 | | 0.07 | | 0.11 | |

Odds Ratios for Myocardial Infarct by VDR allele I genotype [95% CI]

Crude

| | | | | |
|---|---|---|---|---|
| Reference | 1.00 | 1.00 | 1.00 | |
| Heterozygotes | 1.07 [0.72–1.71] | 1.86 [0.90–3.85] | 1.23 [0.86–1.76] | |
| Homozygotes | 1.28 [0.80–2.05] | 2.48 [1.15–5.39] | 1.53 [1.03–2.21] | |
| per copy VDR I allele | 1.13 [0.892–1.44] | 1.53 [1.07–2.20] | 1.24 [1.02–1.51] | |

Age-, BMI-adjusted

| | | | | |
|---|---|---|---|---|
| Reference[†] | 1.00 | 1.00 | 1.00 | |
| Heterozygotes | 1.11 [0.72–1.71] | 1.77 [0.85–3.68] | 1.22 [0.85–1.75] | |
| Homozygotes | 1.33 [0.82–2.14] | 2.45 [1.12–5.34] | 1.55 [1.04–2.30] | |
| per copy VDR I allele | 1.15 [0.91–1.47] | 1.53 [1.06–2.22] | 1.25 [1.02–1.52] | |

[†]"Reference" includes VDR genotypes 22, 23, 33; "Heterozygotes" includes 12, 13; "Homozygotes" includes 11

TABLE 3

Myocardial Infarction According to VDR allele 1 Genotype by Quartiles of Dietary Calcium Intake

| | <877 mg/day | | >877, <1076 | | >1076, <1302 | | ≥1302 | |
|---|---|---|---|---|---|---|---|---|
| | MI (%) | Total | MI (%) | Total | MI (%) | Total | MI (%) | Total |
| Total | 43 (10.) | 432 | 50 (11.6) | 431 | 45 (10.4) | 432 | 49 (11.4) | 430 | by VDR allele 1 genotype

| | | | | | | | | |
|---|---|---|---|---|---|---|---|---|
| Reference[†] | 13 (9.9) | 131 | 14 (12.5) | 112 | 12 (9.6) | 125 | 3 (2.6) | 114 |
| Heterozygores | 21 (10.5) | 200 | 24 (11.8) | 204 | 21 (10.0) | 210 | 26 (12.6) | 207 |
| Homozygotes | 9 (8.9) | 101 | 12 (10.4) | 115 | 12 (12.4) | 97 | 20 (18.3) | 109 |
| $\chi^2$ | 0.19 | | 0.25 | | 0.53 | | 14.17 | |
| P-VALUE | 0.91 | | 0.88 | | 0.77 | | 0.0008 | |

Odds Ratios for Myocardial Infarction by VDR allele 1 genotype [95% Cl]

Crude

| | | | | |
|---|---|---|---|---|
| Reference | 1.00 | 1.00 | 1.00 | 1.00 |
| Heterozygotes | 1.09 [0.52–2.27] | 0.93 [0.46–1.89] | 1.04 [0.49–220] | 5.40 [1.59–18.3] |
| Homozygotes | 0.90 [0.37–2.20] | 0.82 [0.36–1.87] | 1.32 [0.56–3.09] | 8.31 [2.39–29.0] |

[†]"Reference" includes VDR genotypes 22, 23, 33; "Heterozygotes" includes 12, 13; "Homozygotes" includes 11

TABLE 4

Myocardial Arrythmias According to VDR allele 1 Genotype by Quartiles of Dietary Calcium Intake

| | <877 mg/day | | >877, <1076 | | >1076, <1302 | | ≥1302 | |
|---|---|---|---|---|---|---|---|---|
| | MA (%) | Total | MA (%) | Total | MA (%) | Total | MA (%) | Total |
| Total | 37 (12.1) | 307 | 27 (9.2) | 292 | 17 (5.6) | 302 | 31 (10.1) | 306 | by VDR allele 1 genotype

| | | | | | | | | |
|---|---|---|---|---|---|---|---|---|
| Reference[†] | 16 (17.0) | 94 | 6 (8.8) | 68 | 7 (7.7) | 91 | 5 (5.7) | 88 |
| Heterozygotes | 14 (10.1) | 138 | 14 (10.1) | 138 | 6 (4.4) | 135 | 12 (8.5) | 141 |
| Homozygotes | 7 (9.3) | 75 | 7 (8.1) | 86 | 4 (5.3) | 76 | 14 (18.2) | 77 |
| $\chi^2$ | 3.19 | | 0.27 | | 1.11 | | 7.80 | |
| P-VALUE | 0.20 | | 0.87 | | 0.58 | | 0.02 | |

TABLE 4-continued

Myocardial Arrythmias According to VDR allele 1 Genotype by Quartiles of Dietary Calcium Intake

| | ≤877 mg/day | | >877, <1076 | | >1076, <1302 | | ≥1302 | |
|---|---|---|---|---|---|---|---|---|
| | MA (%) | Total | MA (%) | Total | MA (%) | Total | MA (%) | Total |

Odds Ratios for Myocardial arrythmias by VDR allele 1 genotype [95% Cl]

Crude

| | | | | |
|---|---|---|---|---|
| Reference | 1.00 | 1.00 | 1.00 | 1.00 |
| Heterozygotes | 0.57 [0.26–1.23] | 1.13 [0.41–3.12] | 0.54 [0.18–1.69] | 1.60 [0.54–4.74] |
| Homozygotes | 0.51 [0.20–1.32] | 0.92 [0.29–2.92] | 0.69 [0.19–2.46] | 3.63 [1.22–10.9] |

†"Reference" includes VDR genotypes 22, 23, 33; "Heterozygotes" includes 12, 13; "Homozygotes" includes 11

REFERENCES

1. Marian A J. Genetic risk factors for myocardial infarction. Curr Opin Cardiol 1998;13:171–178.
2. Weiss E J, Bray P F, Tayback M, et al. A polymorphism of a platelet glycoprotein receptor as an inherited risk factor for coronary thrombosis. New Engl J Med 1996;334:1090–1096.
3. Iacoviello L, Di Castelnuovo A, de Knijff P, et al. Polymorphisms in the coagulation factor VII gene and the risk of myocardial infarction. New Engl. J Med 1998;338:79–85.
4. Kuivenhoven J A, Jukema W, Zwinderman A H, et al. The role of a common variant of the cholesteryl ester transfer protein gene in the progression of coronary atherosclerosis. New Engl. J Med 1998;338:86–93.
5. Lind L, Skarfors E, Berglund L, Lithell H, and Ljunghall. Serum calcium: a new, independent, prospective risk factor for myocardial infarction in middle-aged men followed for 18 years. J Clin Epidemiol 1997;50:967–973.
6. Haussler M R, Haussler C A, Jurutka P W, et al. The vitamin D hormone and its nuclear receptor: molecular actions and disease states. J Endocrinol 1997;154:S57–S73.
7. Scragg R, Jackson R, Holdaway I M, Lim T, and Beaglehole R. Myocardial infarction is inversely associated with plasma 25-hydroxyvitamin D3 levels: a community based study. Int J Epidemiol 1990;19:559–563.
8. Brunvand L, Haga P, Tangsrud S E, and Haug E. Congestive heart failure caused by vitamin D deficiency? Acata Paediatr 1995;84:106–108.
9. Vintzileos A M, Campbell W A, Soberman S M, and Nochimson D J. Fetal atrial flutter and X-linked dominant vita D resistant rickets. Obstet Gynecol. 1985;65:39S–44S.
10. Kessel L. Sick sinus syndrome cured by . . . vitamin D? Geriatrics 1990;45:83–85.
11. Cooper G S, Umbach D M. Are vitamin D receptor polymorphisms associated with bone density? J Bone Miner Res 1996;11:1841–9.
12. Carling T. Kindmark A, Helleman P, et al. Vitamin D receptor genotypes in primary hyperparathyroidism. Nature Med 1995;1:1309–1311.
13. Taylor J A, Hirvonen A, Watson M, Pittman G, Mohler J L, and Bell D A. Association of prostate cancer with vitamin D receptor gene polymorphism. Canc. Res. 1996;56:4108–4110.
14. Uitterlinden A G, Burger H, Huang Q, et al. Vitamin D receptor genotype is associated with radiographic osteoarthritis at the knee. J Clin Invest 1997;100:259–263.
15. Hoffman A, Grobbee D E, de Jong, P T V M, van den Ouweland F A. Determinants of disease and disability in the elderly: the Rotterdam Elderly Study. Eur J Epiderniol 1991;7:403–22.
16. Uitterlinden A G, Pols H A P, Burger H, et al. A large scale population based study of the association of vitamin D receptor gene polymorphisms with bone mineral density. J Bone Miner Res 1996;11:1242–1248.
17. O'Connell T D, Weishaar R E, and Simpson R U. Regulation of myosin isozyme expression by vitamin D3 deficiency and 1,25-dihydroxy vitamin D3 in the rat heart. Endocrinology 1994; 134: 899–905
18. Weishaar R E, Kim S N, Saunders D, and Simpson R U. Involvement of vitamin D3 with cardiovascular function III. Effects on physical and morphological properties. Am J Physiol 1990;258 (Endocrinol. Metab. 21):E134–E142.
19. Weishaar R E, and Simpson R U. Involvement of vitamin D3 with cardiovascular function II. Direct and indirect effects. Am J Physiol 1987;253 (Endocrinol. Metab. 16):E675–E683.
20. Weishaar R E, and Simpson R U. Vitamin D3 and cardiovascular function in rats. J Clin Invest 1987;79:1706–1712.
21. Psaty B M, Heckbert S R, Koepsell T D, et al. The risk of myocardial infraction associated with antihypertensive drug therapies. JAMA 1995; 271:620–625.
22. Michalewicz L, and Messerli F H. Cardiac effects of calcium antagonists in systemic hypertension. Am J Cardiol. 1997; 79:39–46.

What is claimed is:

1. A method of predicting the response of a human subject to treatment with calcium, said method comprising the step of analysing genetic material of a human subject to determine whether a baT haplotype of a vitamin D receptor gene is present in the subject, wherein the presence of the baT haplotype is indicative that the subject will react adversely to treatment with the ingestion of at least 1302 mg/day of calcium.

2. A method according to claim 1 wherein said subject is first diagnosed as being susceptible to heart disease.

3. A method according to claims 1 or 2 further comprising administering the appropriate treatment to the subject.

4. A method according to claim 2 wherein the subject is diagnosed as being susceptible to heart disease by a method comprising analyzing genetic material of a subject to determine whether the baT haplotype is present, wherein the presence of the baT haplotype is indicative of an increased susceptibility to heart disease.

* * * * *

UNITED STATES PATENT AND TRADEMARK OFFICE
CERTIFICATE OF CORRECTION

PATENT NO. : 6,808,881 B1
DATED : October 26, 2004
INVENTOR(S) : A.G. Uitterlinden et al.

It is certified that error appears in the above-identified patent and that said Letters Patent is hereby corrected as shown below:

Title page,
Item [30], Foreign Application Priority Data, "9819764" should read -- 9819764.3 --
Item [56], References Cited, FOREIGN PATENT DOCUMENTS, delete first occurrence of "WO9740187 A"
OTHER PUBLICATIONS, "O'Connell, T.D. et al.," reference, "1,25-dihydrox-yvitamin" should break -- 1,25-dihyroxy-vitamin --
Item [74], *Attorney, Agent or Firm*, "O'Connor:" should read -- O'Connor --
After Item [57], ABSTRACT, "4 Claims, 5 Drawing Sheets" should read -- 4 Claims, 1 Drawing Sheet --

Drawings,
Delete drawings 1 of 5, 2 of 5, 3 of 5 and 4 of 5 and rename drawings "Sheet 5 of 5" to -- Sheet 1 of 1 --

Column 1,
Line 24, "arrythmnias" should read -- arrhythmias --
Line 37, "it's" should read -- its --
Line 49, "hean" should read -- heart --
Line 52, ""arrythria" should read -- arrhythmia --
Line 55, "caucasian" should read -- Caucasian --
Line 59, "contracile" should read -- contractile --
Line 61, "via" should read -- vitamin --

Column 2,
Line 5, "arrythmia" should read -- arrhythmia --
Line 16, "gene. as" should read -- gene, as --

Column 3,
Line 11, "arrythmina," should read -- arrhythmia, --
Line 57, "et al" should read -- et al. --

Column 4,
Line 3, "for example" should read -- for example, --
Line 22, "RFLP analysis" should read -- RFLP analysis. --
Line 35, "et al[16]." should read -- et al.[16] --

UNITED STATES PATENT AND TRADEMARK OFFICE
CERTIFICATE OF CORRECTION

PATENT NO.    : 6,808,881 B1
DATED         : October 26, 2004
INVENTOR(S)   : A.G. Uitterlinden et al.

It is certified that error appears in the above-identified patent and that said Letters Patent is hereby corrected as shown below:

Column 5,
Line 1, before the sequence ID string, insert -- 1. --
Line 2, after the sequence ID string, delete "1."
Line 5, before the sequence ID string, insert -- 2. --
Line 5, after the sequence ID string, delete "2."
Line 18, "may in" should read -- may be in --
Line 39, "diseases may" should read -- diseases, may --
Line 61, "gene, may" should read -- gene may --

Column 6,
Line 1, "techniques for" should read -- techniques, for --
Line 4, "for example" should read -- for example, --
Line 17, "arrythmia" should read -- arrhythmia --
Line 27, "samples, for" should read -- samples for --
Line 35, "FIGURE:" should read -- Figure: --
Line 42, "arrythmias" should read -- arrhythmias --
Line 65, "arrytmias" should read -- arrhythmias --

Column 7,
Line 1, "included and" should read -- included an --
Line 16, "so called" should read -- so called --
Line 26, "arrythmias" should read -- arrhythmias --
Line 35, "die" should read -- the --
Line 46, "10 mnM" should read -- 10 mM --
Line 53, "inin" should read -- min --
Line 55, "BsamI," should read -- BsmI, --
Line 57, "inM" should read -- mM --
Lines 58 and 61, "MM" should read -- mM --
Line 61, "mnM" should read -- mM --

Column 8,
Line 9, "allele1" should read -- allele 1 --
Lines 14, 17 and 22, "arrythmias." should read -- arrhythmias. --
Line 17, "arrythrnias." should read -- arrhythmias. --
Line 30, "Anthropometric," should read -- Anthropometric --

Column 9,
Line 16, "arrytmias" should read -- arrhythmias --
Line 19, "arrythrnias" should read -- arrhythmias --

UNITED STATES PATENT AND TRADEMARK OFFICE
CERTIFICATE OF CORRECTION

PATENT NO. : 6,808,881 B1
DATED : October 26, 2004
INVENTOR(S) : A.G. Uitterlinden et al.

It is certified that error appears in the above-identified patent and that said Letters Patent is hereby corrected as shown below:

Column 10,
Line 3, "arrythmnias." should read -- arrhythmias. --
Line 3, "arrhythmias" should read -- arrhythmias --
Line 6, "observe, is" should read -- observed is --
Lines 7 and 33, "observe" should read -- observed --
Line 10, "arrythmias." should read -- arrhythmias. --
Line 12, "arrythmias" should read -- arrhythmias --
Line 14, "suggest" should read -- suggests --
Lines 16 and 18, "arrythmias" should read -- arrhythmias --
Line 29, "arrythmias," should read -- arrhythmias, --
Line 46, "3.91" should read -- 0.91 --

Column 11,
Line 9, "Infaret" should read -- Infarct --
Line 9, "CI]" should read -- Cl] --
Line 12, "]0.86-1.76]" should read -- [0.86-1.76] --
Line 30, "Heterozygores" should read -- Heterozygotes --

Column 13,
Line 5, "arrythmias" should read -- arrhythmias --
Line 50, "vita" should read -- vitamin --

Column 14,
Line 17, "Carling T." should read -- Carling T, --
Line 30, "Epiderniol" should read -- Epidemiol --
Line 38, "1,25-dihydroxy vitamin" should read -- 1,25-dihydroxyvitamin --

Signed and Sealed this

First Day of February, 2005

JON W. DUDAS
*Director of the United States Patent and Trademark Office*